United States Patent [19]

de Farias

[11] 4,159,019

[45] Jun. 26, 1979

[54] INSTRUMENT FOR USE IN TAKING OCULAR TENSION MEASUREMENTS BY THE TONOMETRIC METHOD OF OCULAR DEPRESSIONS

[76] Inventor: Natalicio L. de Farias, Rua General, Glicerio 355/1.104, Rio de Janeiro, Brazil

[21] Appl. No.: 784,030

[22] Filed: Apr. 4, 1977

Related U.S. Application Data

[63] Continuation-in-part of Ser. No. 625,579, Oct. 24, 1975, abandoned.

[30] Foreign Application Priority Data

Oct. 31, 1974 [BR] Brazil ..................................... 9137

[51] Int. Cl.² ............................................. A61B 3/00
[52] U.S. Cl. .................................................. 128/645
[58] Field of Search .............. 128/2 T, 2 R, 9; 73/80; 351/2, 6, 7; 46/1 F

[56] References Cited

U.S. PATENT DOCUMENTS

| 631,227 | 8/1899 | Peppard | 351/2 X |
|---|---|---|---|
| 2,724,305 | 11/1955 | Brandt | 351/7 |
| 2,757,574 | 8/1956 | Thorbum | 351/6 X |
| 3,452,589 | 7/1969 | Hargens et al. | 73/80 |
| 3,511,085 | 5/1970 | Posner et al. | 73/80 |
| 3,690,158 | 9/1972 | Lichtenstein et al. | 128/2 T X |
| 3,756,073 | 9/1973 | Lavallee et al. | 73/80 |

FOREIGN PATENT DOCUMENTS 1535696 7/1968 France ..................................... 128/2 T
426652 1/1975 U.S.S.R. ................................... 128/2 T

OTHER PUBLICATIONS

Emarah, "Simplified Indirect Opththalmoscope", Brit. J. Ophthal., 1964, 48, pp. 176–178.
Coleman et al., "A New System . . . Using Ultrasound", Arch. of Ophth., vol. 77, Jan. 1967, pp. 124–127.

Primary Examiner—Lee S. Cohen
Attorney, Agent, or Firm—Orville N. Greene; Frank L. Durr

[57] ABSTRACT

This disclosure relates to an instrument for use in taking ocular tension measurements by the tonometric method of ocular depression which instrument may be called a tonoscope. The tension measurements, per se, may be made with a tonometer such as Schiotz's tonometer. The tonoscope is provided with, a head piece which may be attached to the patients forehead just above the eyes, a cone adjustably attached to the headpiece to project in front of the right or left eye of the patient and, preferably, an adjustable shade which is movable to temporarily extend in front of the eye on which the pressure is to be measured. Preferably, also, the adjustable cone contains a scale cooperating with a pointer on the headpiece to indicate the angle to which the axis of the cone projects.

7 Claims, 3 Drawing Figures

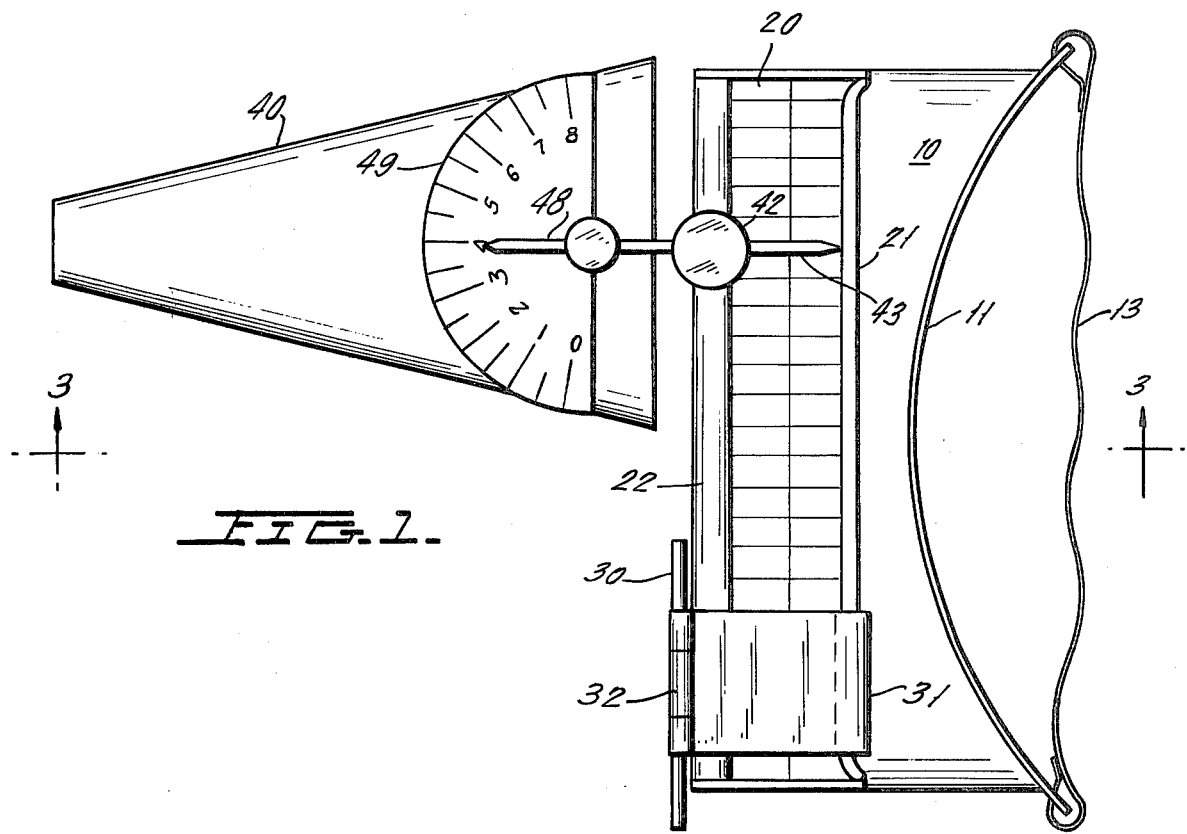
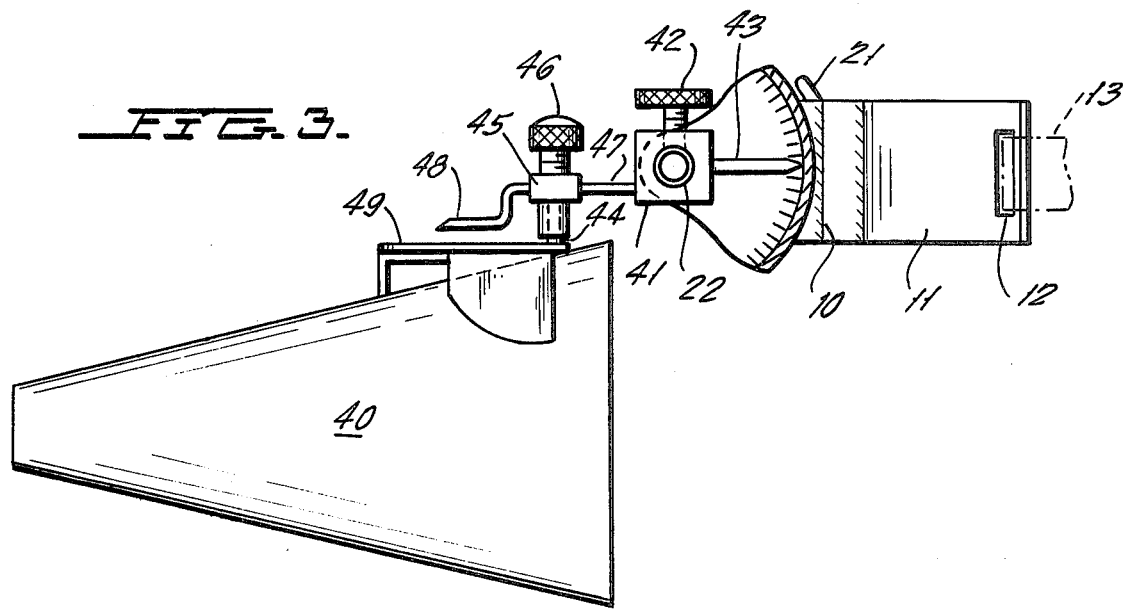

INSTRUMENT FOR USE IN TAKING OCULAR TENSION MEASUREMENTS BY THE TONOMETRIC METHOD OF OCULAR DEPRESSIONS

This application is a continuation-in-part of application Ser. No. 625,579 filed Oct. 24, 1975, now abandoned.

BACKGROUND OF THE INVENTION

The invention relates to a device for enabling a doctor or other skilled operator to obtain correct pressure readings of a tonometer.

About one hundred and fifty years ago the increase of eye pressure was found to be related to glaucoma, a disease with high index of blindness. It was not until the beginning of the 19th century that the first excellent description of glaucoma with raised ocular tension was given by Antoine Demours. He noticed that "le globe oculaire devient dur au toucher" (Duke Elder-System of Ophthalmology—vol. XL—1969).

With this observation, the first method of verifying ocular pressure appeared, which was effected by depression of the eye by the fingers of the examiner. This method, in use until today, is not precise and does not offer reliable means of information.

In 1905 Schiotz discovered the mechanical tonometer bearing his name. It is able to reveal in millimeters of mercury the pressure encountered. However, the mobility of the eye does not permit that repeated pressure readings in the course of the diagnosis or treatment of the glaucoma be carried out under equal conditions of the eye, as scientific research demands, giving rise to different interpretations among researchers.

The present invention complements pressure readings by the Schiotz tonometer, which can be carried out in one and the same eye and can be registered for subsequent comparison.

This invention offers tranquility to the patient who does not feel nor percieve the taking of the pressure; it facilitates also the technique of the physician, assuring scientific rigor in the research. Other tonometers have been submitted, like those of Gradle, McLean Sunter, Harrington, Goldman, Lichtenstein and others, —all of them with the object of discovering minimum pressures in the course of a beginning glaucoma. On the other hand, the inaccuracy of the results obtained have been connected with variable resistance of the ocular globe to the depressing force of the tonometer. In 1939 Friedenwald used a mathematical formula based on the depressing force of the cornea, the depression area, ocular rigidity, cornea identation, and founded the method of simple differential tonometry. In 1959 Goldman created his Applanation Tonometer ("Tonometro de Aplanacao"), reducing the depression area of the cornea to a diameter of 3.06 mm, with 200 Micrometers of cornean indentation. In 1967, Lichtenstein, using acoustic energy reduced the indentation of the cornea to 2.5 micrometers. These outstanding researchers, by employing the method of ocular depression with the aid of mechanical means (original discovery of Schiotz), made use of mathematical calculations applied to biological processes, which led to disagreement in the interpretation of the results. "The computation is a good example of difficulty and danger of expressing biological processes in terms of mathemetical equations with their deceptive aura of accuracy"—Duke Elder—System of Ophthalmology—vol. XL—1969.

Reverting to the first studies of Schiotz, the present inventor tried to give more precision and scientific accuracy to the reading of ocular pressure by the tonometer of Schiotz, to map the results by degrees, to connect them by causes and effects, deducting and concluding. He followed the inductive method of experimental science—instead of the mathematical demonstrative method. Hence, this invention of the principle of registration of the position of the eye examined during repeated pressure readings which readings are to be related, creates a valuable instrument for experimental science.

The object of this invention is to provide a method and an apparatus to complement the reading of ocular pressure by the tonometer of Schiotz or similar ones. Other objects are to allow for measurement with entire comfort of the examined person, which latter does not feel nor perceive the mechanical contact with the cornea. A principle of this invention is to register the position of the eye, when pressue is taken, by the Schiotz method of ocular depression or similar ones, whereby a physical system immobilizes the eye under examination.

The fixation reflex of the eyes is maintained by the center of psycho-motive reflexes. It coordinates the ocular muscles moving the two eyes as if they were just one eye. The excitation of the retina of the fixing eye brings about the mechanism of association of the two eyes in a certain position, maintaining the examined eye immovable. This position can vary in vertical, horizontal, oblique and rotating direction thanks to an extremely delicate motive mechanism directed by will power. Thus, while the patient immovably fixes a given point in space (for instance the ceiling of the examination room) through the central hole of the cone, the other eye, which is being examined, also remains immovable by virtue of the fixation reflex. Once an adequate position has been arrived at by movements in the cone around the control system of eye movement, and when the desired position of the eye has been reached, ocular pressure is measured by the tonometer of Schiotz and the position of the eye is registered.

The objects of the invention are attained by providing a head piece adapted to fit on the forehead above the eyes, to which headpiece is attached a hollow cone open at both ends, the position of the cone being adjustable so that its area extends at various angles in a direction away from the eye with the larger opening of the cone nearest the eye, whereby, depending on the position of the cone, the eye can view a point or small area defined by the smaller opening in the cone. Preferably the cone is adjustable laterally to be positioned in front of either the right or the left eye and is also pivotable in a horizontal as well as in a vertical direction to fix the eye in a variety of positions. Once the position of one eye is fixed by the cone, the other eye is also fixed in a corresponding position and the tonometer reading is taken on said other eye.

For a complete understanding of the invention, reference is made to the accompanying drawing illustrating a preferred embodiment, but it will be understood that the invention may be otherwise embodied within the scope of my broader claims. In the drawings:

FIG. 1 is a top plan view of the tonoscope of the invention.

FIG. 3 is a sectional view taken on line 3—3 of FIG. 1.

Figure 2:
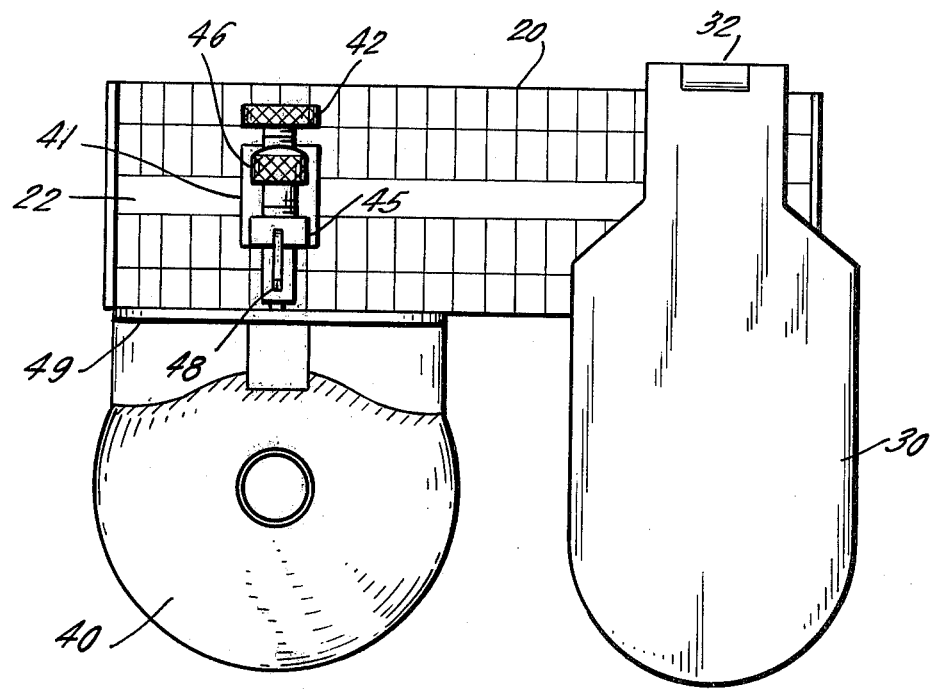
FIG. 2 is a front view of the tonoscope of the invention.

The tonoscope comprises a headpiece 10, the rear side of which is provided with a curved flat surface 11 adapted to fit comfortably on the forehead of a patient. The headpiece has side openings 12 to which an elastic or similar band 13 is attached for holding the head piece firmly in place. The front end of the head piece 10 is provided with an arcuate scale piece 20 extending horizontally with respect to the patient, and also horizontally extending tubes or rods 21 and 22.

Slidably and pivotally mounted on the rod 21 is the eyeshade 30 which is connected to the rod 21 by means of a hinge 31 and also includes an intermediate hinge joint 32 so that it can be moved to the position shown in FIG. 1 or 2 in front of the eye for conducting the testing. The eyeshade can be slid along rod 21 to a position on the opposite side of the headpiece.

Slidably and pivotally mounted on the tube or rod 22 is the tubular cone device 40. This cone device 40 is mounted so that its axis extends generally forwardly, but in a region below the headpiece 10 and generally on a level with the eyes. Since the larger opening of the cone 40 is nearest the eye, it is not essential that the axis of the cone always be in direct alignment with the eye. The cone 40 is pivotal in a vertical direction since the bearing block 41 is pivotally mounted on the tube 22 and can be temporarily fixed in any position with respect to axle 44 by set screw 46. The tube 45 is secured to bearing block 41 by means of the rod 47 and said tube 45 also has a pointer 48 projecting from tube 45 to indicate on the scale, the angle which the axis of the cone 40 is set.

In operation, the patient is placed in a reclining position on his back and care is taken not to compress the neck veins, the patients eyes are anaesthetized, the headpiece is attached and the pointers 43 and 48 positioned at a selective place. The patient is instructed to look through the cone 40 with one eye while the other eye is covered by the shade 30. Thereafter, the shade 30 is pivoted to a neutral position and the measurement is taken with a tonometer on the one eye, while the other eye fixes the position of the eye being measured by peering through the opening in the cone 40. The readings on scales 20 and 49 are recorded for future comparisons. When all desired measurements are taken in one eye, the shade 30 and cone 40 are slid to opposite sides of the headpiece and measurements are taken on the other eye. The tonometer is usually equipped with a series of replaceable weights and the usual skills and precautions of the physician or other operator are used in taking the measurements.

What I claim is:

1. A tonoscope for use with a tonometer to take pressure measurements on particular parts of the eyeball comprising
   a headpiece,
   means for attaching the headpiece to the forehead of a patient,
   a single hollow cone having openings at both the larger and smaller ends thereof so as to allow unimpeded viewing therethrough,
   means for adjustably suspending the cone from the headpiece when the headpiece is connected to the forehead of the patient so that the axis of the cone is in general alignment with one of the eyes of a patient with the opening in the smaller end of said cone extending away from the headpiece, said hollow cone and its suspending means being so constructed as to leave the other eye exposed for testing.

2. The tonoscope as claimed in claim 1 wherein the means for suspending the cone from the headpiece comprises a horizontal linear member attached to and extending the width of the headpiece, said suspending means including a bearing block slidably mounted on said horizontal linear member and means in said bearing block for fixing the block in any desired position on said linear member, said cone being connected to said bearing block.

3. The tonoscope as claimed in claim 2 wherein said bearing block is also pivotally mounted on said horizontal linear member.

4. The tonoscope as claimed in claim 3 comprising scale means on the headpiece and pointer means on the bearing block associated with said scale means to indicate the pivotal position of the block with respect to the linear member.

5. The tonoscope as claimed in claim 2 wherein the means for suspending the cone from the headpiece comprises an axle fixed to the outer surface of the hollow cone, and tubular means for pivotally mounting the axle for movement about an axis substantially at right angles to the axis of the hollow cone, said tubular means being connected to said bearing block.

6. The tonoscope as claimed in claim 5 comprising pointer means on said tubular means and scale means on said hollow cone cooperating with said pointer means to indicate the angular position of the cone axis with respect to the headpiece.

7. The tonoscope as claimed in claim 2 comprising means for suspending an eyeshade in front of said other eye, said means for suspending an eyeshade including a horizontal rod mounted on said headpiece parallel to but in spaced relation to the horizontal linear member, and an eyeshade slidably hinged to said horizontal rod.

* * * * *